US012496404B2

(12) United States Patent
Peterson et al.

(10) Patent No.: US 12,496,404 B2
(45) Date of Patent: Dec. 16, 2025

(54) SYRINGE HAND GRIP ADAPTER

(71) Applicants: Donald Russell Peterson, Saint Charles, IL (US); John W. Birk, West Hartford, CT (US); Simon Kudernatsch, Saint Charles, IL (US)

(72) Inventors: Donald Russell Peterson, Saint Charles, IL (US); John W. Birk, West Hartford, CT (US); Simon Kudernatsch, Saint Charles, IL (US)

( * ) Notice: Subject to any disclaimer, the term of this patent is extended or adjusted under 35 U.S.C. 154(b) by 732 days.

(21) Appl. No.: 17/929,371

(22) Filed: Sep. 2, 2022

(65) Prior Publication Data

US 2024/0075212 A1 Mar. 7, 2024

(51) Int. Cl.
*A61M 5/31* (2006.01)

(52) U.S. Cl.
CPC ... *A61M 5/3137* (2013.01); *A61M 2005/3139* (2013.01)

(58) Field of Classification Search
CPC .................... A61M 5/3137; A61M 2005/3139
USPC ........................... 433/82, 85; 222/465.1, 386
See application file for complete search history.

(56) References Cited

U.S. PATENT DOCUMENTS 4,643,724 A * 2/1987 Jobe ........................ A61M 5/24 604/232
5,115,816 A 5/1992 Lee
6,719,735 B1 4/2004 Gammon
7,611,495 B1 11/2009 Gianturco
9,339,606 B2 5/2016 Evans et al.
11,464,910 B1 * 10/2022 Merson ............. A61M 5/31576
2002/0087125 A1 * 7/2002 Pokorney ........... A61M 5/31511 604/227
2003/0060777 A1 * 3/2003 Benz ................... A61M 5/3135 604/227
2003/0097115 A1 * 5/2003 Gruenberg ........ A61M 5/31513 604/226
2004/0034323 A1 * 2/2004 Manthey ............. A61M 5/3243 604/198
2006/0173415 A1 8/2006 Cummins
(Continued)

FOREIGN PATENT DOCUMENTS

JP 2007175444 A * 7/2007 .......... A61M 5/3137
WO WO-2024008948 A1 * 1/2024 ............... A61L 2/20

OTHER PUBLICATIONS

JP-2004175444 A (Year: 2007).*

*Primary Examiner* — Cris L. Rodriguez
(74) *Attorney, Agent, or Firm* — McHale & Slavin, P.A.

(57) ABSTRACT

A hand grip adapter for a syringe formed from a body having a first end wall and a second end wall with a support base therebetween. The support base includes a centrally disposed receptacle for receipt of a syringe flange. The first end wall formed perpendicular to the support base having a curvature outer surface to conform to the palm of an individual's hand. The second end wall is formed parallel to the first end wall and includes four finger depressions wherein an individual can place their index, middle, ring, and little finger. At least one of the depressions includes a rim forming a circular opening for ease of grasping. The first side wall is configured to rest in the palm of an individual's hand and said second end wall is configured to receive the finger tips from the individual's hand with a syringe secured in the support base.

16 Claims, 10 Drawing Sheets

(56) References Cited

U.S. PATENT DOCUMENTS

| | | | | |
|---|---|---|---|---|
| 2016/0166770 | A1* | 6/2016 | Salas | A61M 5/3137<br>604/192 |
| 2018/0311432 | A1* | 11/2018 | Vardi | A61M 5/31513 |
| 2019/0346061 | A1* | 11/2019 | Shiner | B25B 13/48 |
| 2020/0016331 | A1* | 1/2020 | Lee | A61M 5/14546 |
| 2020/0268363 | A1* | 8/2020 | Odintsov | A61B 10/0045 |
| 2021/0038820 | A1* | 2/2021 | Alsuhaibani | A61M 5/3148 |
| 2021/0077738 | A1* | 3/2021 | Dadachanji | A61M 5/31513 |
| 2024/0198006 | A1* | 6/2024 | Groop | A61M 5/3137 |
| 2024/0261509 | A1* | 8/2024 | Sanchez | A61M 5/31515 |

* cited by examiner

SYRINGE HAND GRIP ADAPTER

FIELD OF THE INVENTION

The field of the invention is syringe modification and, in particular, in particular, to a syringe hand grip adapter for increased control of volume ejection.

BACKGROUND OF THE INVENTION

The use of a staining dye agent to enhance medical images is well known. This technique involves injecting the staining dye into a patient for a chromoendoscopy procedure used in identifying problematic regions during various diagnostic procedures. The staining method is utilized during screening endoscopy to diagnose intestinal metaplasia, gastric cancer, duodenal and colonic disease. The staining dye distinguishes different types of cell layers to improve the recognition of surface patterns by enhancing the contracts of raised and deepened areas.

The ability to infuse precise volumes of radiological contrast agents is critical for Endoscopic Retrograde Cholangiopancreatography, an endoscopic procedure wherein a risk of pancreatitis can be caused by excessive infusion volumes. The staining and contrast agent infusion is typically administered using standard 12 ml or 10 ml syringes with an add-on option of various thumb and finger grips. These grips are intended to increase control and ability to push during the infusion while maintaining the standard three-finger syringe grip. However, the three-finger grip engages the entire wrist during the ejection phase, potentially decreasing the accuracy in applications where precise and small volumes are needed.

U.S. Pat. No. 6,719,735 discloses a hand grip adapter for use with a syringe. The adapter having legs secured to a thumb compression member to cause the legs to depend from the thumb compression member and brackets secured to the distal ends of said legs to receive the flange of the cylindrical body of the syringe.

U.S. Pat. No. 5,115,816 discloses a single-hand controlled aspirating device having a syringe barrel, a plunger operative in the barrel, and a finger grip assembly that is mounted to the syringe barrel and plunger for controlling plunger movement within the barrel. The finger grip assembly includes a body member and a trigger member slidably engaged within the body member.

U.S. Patent Publication discloses a syringe adaptor for use in maintaining a plunger in a fixed position relative to a barrel of a surgical syringe. A syringe adaptor is provided having a body that is adapted to mate to a plunger on a syringe, and at least one extension that extends from the body and that is adapted to releasably engage a portion of a barrel on the syringe to hold the plunger in a fixed position relative to the barrel. When the body is mated to a plunger on a syringe, the body can be adapted to move between a first position in which the at least one extension is adapted to engage a portion of the barrel, and a second position in which the body and plunger are freely movable relative to the barrel.

U.S. Pat. No. 9,339,606 discloses an attachment member configured to be removably mounted onto the syringe barrel flange, and a flange member pivotably attached to the attachment member. At least a portion of the flange member is pivotable between a use position, wherein said portion of the flange member extends generally perpendicular to the syringe barrel, thereby providing a flange having a greater extent than the syringe barrel flange, and a non-use position, wherein said portion of the flange member does not extend generally perpendicular to the syringe barrel.

U.S. Pat. No. 7,611,495 discloses an injection retarder for reducing the rate of delivery of a hand-held hypodermic syringe. The injection retarder a thumb tip rest is provided against which the thumb may be braced, thereby providing additional mechanical advantage and finer control of the rate of injection. Alternatively, a set of teeth and an opposing mating teeth increase friction and slow the progress of the plunger.

What is needed in the art is a syringe adapter having first end wall configured to rest in the palm of an individual's hand and said second end wall configured to receive the finger tips from the individual's hand with a syringed placed therebetween, whereby the individual may depress said finger base with their thumb allowing a controlled injection of fluid within the syringe with an uninterrupted view of a side of the syringe which increased the ejection volume accuracy by using a thumb control.

SUMMARY OF THE INVENTION

Disclosed is a hand grip adapter for a syringe formed from a support base having a first end wall and a second end wall. The support base includes a receptacle for receipt of a syringe flange. The first end wall formed perpendicular to the support base having a curvature outer surface to conform to the palm of an individual's hand. The second end wall is formed parallel to the first end wall and includes four finger depressions wherein an individual can place their index, middle, ring, and little finger. At least one of the depressions includes a rim forming a circular opening for ease of grasping. The first side wall is configured to rest in the palm of an individual's hand and said second end wall is configured to receive the finger tips from the individual's hand with a syringed placed in said body therebetween. The individual may depress the finger base with their thumb allowing a controlled injection of fluid from the syringe and an uninterrupted view of a side of the syringe.

An objective of the invention is to disclose a syringe adapter that provides an increased control for small volume ejections.

Another objective of the invention is to disclose a syringe adapter that allows an ease of conversion from three-finger grip to palm-held thumb control for any standard size 12 ml and 10 ml syringe.

Still another objective of the invention is to disclose a syringe adapter having a twist-and-lock feature for securing the syringe in place.

Yet still another objective of the invention is to disclose a syringe adapter having a simplistic design that is suitable for bulk manufacturing via injection molding.

Still another objective of the invention is to disclose a syringe adapter that can be used by either left or right handed individuals.

Yet still another objective of the invention is to provide a syringe adapter that low cost to manufacture, disposable or recyclable.

An advantage of the syringe adapter is that a care taker can keep their wrist in the same position wherein the adapter allows the dosage lines to be in more natural view for interpretation in comparison to the three-finger grip which may contribute to a greater volume control even further.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DESCRIPTION OF THE PREFERRED EMBODIMENT

Figure 1:
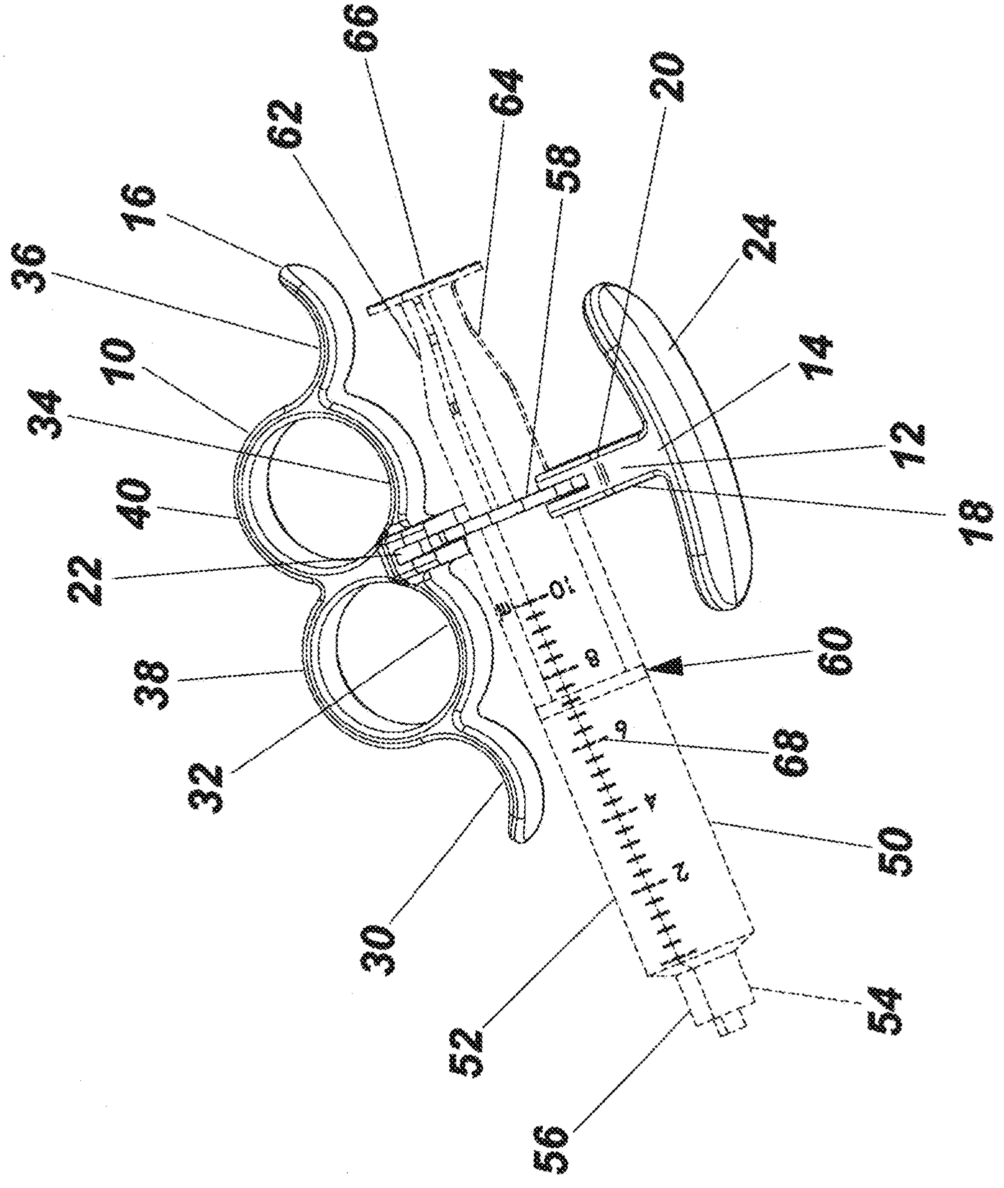
FIG. 1 is a rear perspective view of the syringe hand grip adapter with finger loops holding a syringe.
Figure 2:
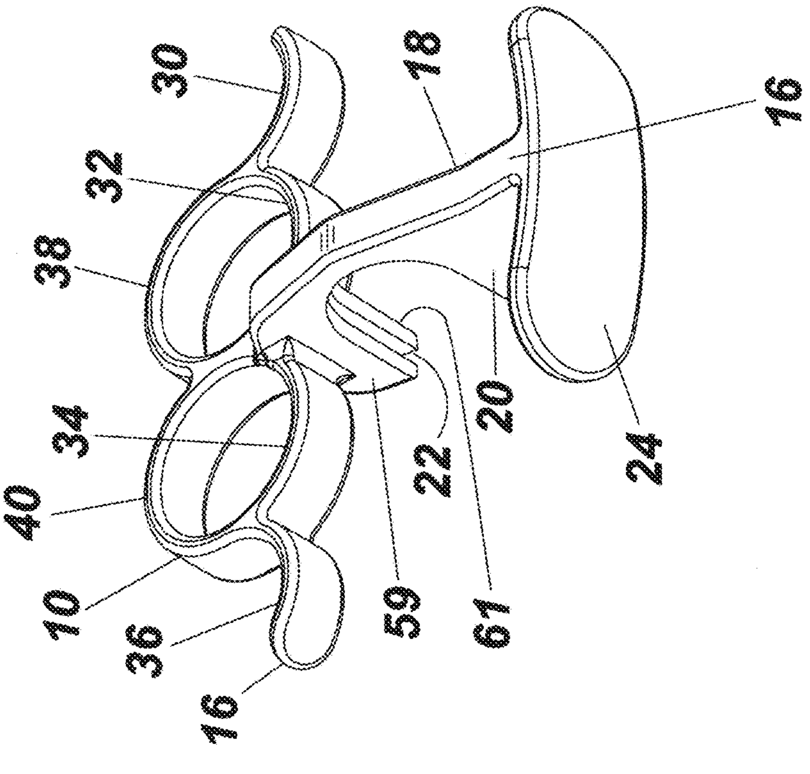
FIG. 2 is a front perspective view of FIG. 1 without the syringe.
Figure 3:
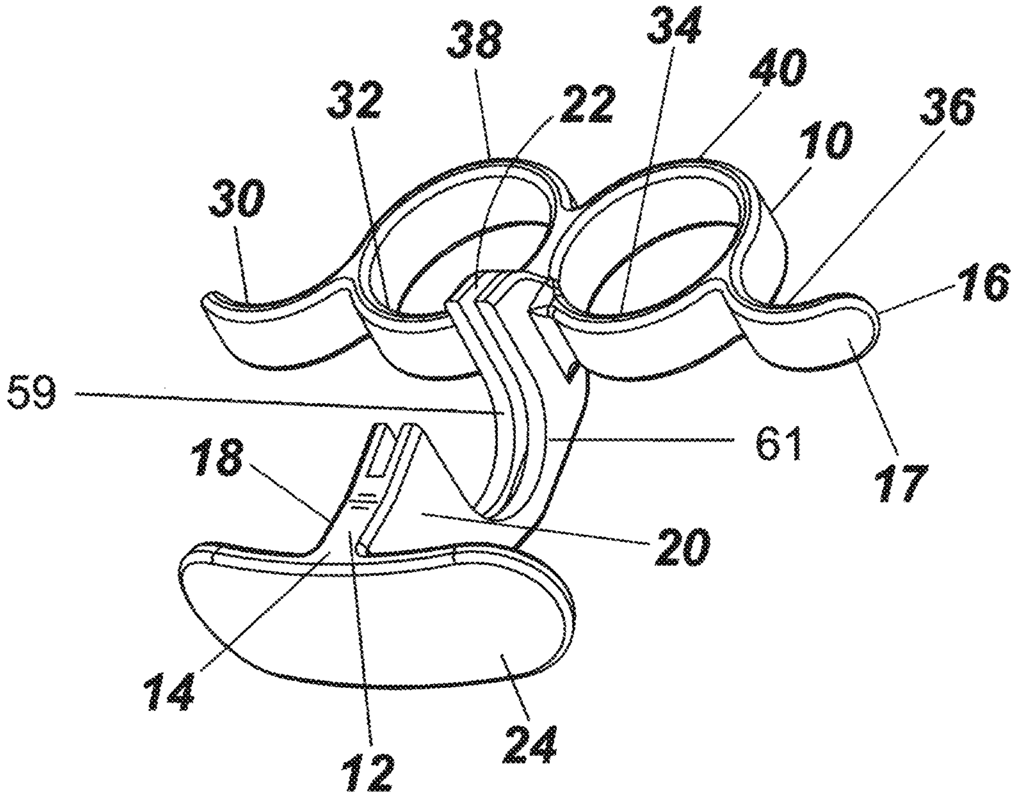
FIG. 3 is a rear perspective view of FIG. 2.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Movements that require engagement of multiple muscles or muscle groups generally tend to be more complex to execute, leaving a larger margin for error. To improve ejection volume accuracy, the instant syringe adapter is palm held and solely utilizes a thumb carpometacarpal (CMC) flexion to depress the syringe plunger, a method commonly used in pipetting and/or micro-pipetting for precise volume control.

Referring to FIGS. 1-3 and 6-9, the hand grip adapter 10 is for used with a syringe 50 having a hollow cylindrical body 52 having an outlet 54 at one end 56 and a laterally extending flange 58 at the opposite end 60. A piston 62 disposed within and adapted for reciprocal movement in the body 52, a shaft 64 attached to the piston 62 and extending outwardly of the body 52 at the opposite end and operative to impart reciprocal movement to the piston 62, and a finger base 66 extending from the shaft 64.

The hand grip adapter 10 comprising a support base 12 having a first end wall 14, a second end wall 16 spaced apart by a bridge 18 having a side wall 20. The support base 12 including a centrally disposed receptacle 22 for receipt of a syringe laterally extending flange 58. The first end wall 14 is formed perpendicular to the support base 12 having a curvature outer surface 24 that conforms to the palm of a human hand. The outer surface 24 is shaped to allow use by left or right handed individuals with a slight curvature that allows positioning in the palm of any size hand. The second end wall 16 is formed parallel to the first end wall 14 having an inner surface with a first depression 30 for receipt of an index digit, a second depression 32 for receipt of a middle digit, a third depression 34 for receipt of a ring digit; and a fourth depression 36 for receipt of a little digit. In a reverse use by a left handed individual, the digits are reversed. In one embodiment, the second depression 32 includes a circular rim 38 and the third depression 34 includes a circular rim 40 termed finger loops. The finger loops allow an individual to hold the adapter 10 without the need of a compression grip. The first side wall 12 is configured to rest in the palm of an individual's hand and the second end wall 16 is configured to receive the finger tips from the individual's hand with a syringe 50 placed in the support base 12 therebetween. The individual may depress the finger base 66 with their thumb allowing a controlled injection of fluid from the syringe 50 and an uninterrupted view of dosage line 68 found on the side of the syringe 50.

The hand grip adapter 10 is designed to fit multiple palm sizes and to provide conformable and secure slip-free grip. The syringe 50 is secured inside of the adapter 10 utilizing a twist-and-lock feature, where a simple twist of the syringe secures it in place safely. This feature accommodates 12 and 10 ml syringes and allows for both, left-handed and right-handed operation without obstructing the dosage line view.

Figure 6:
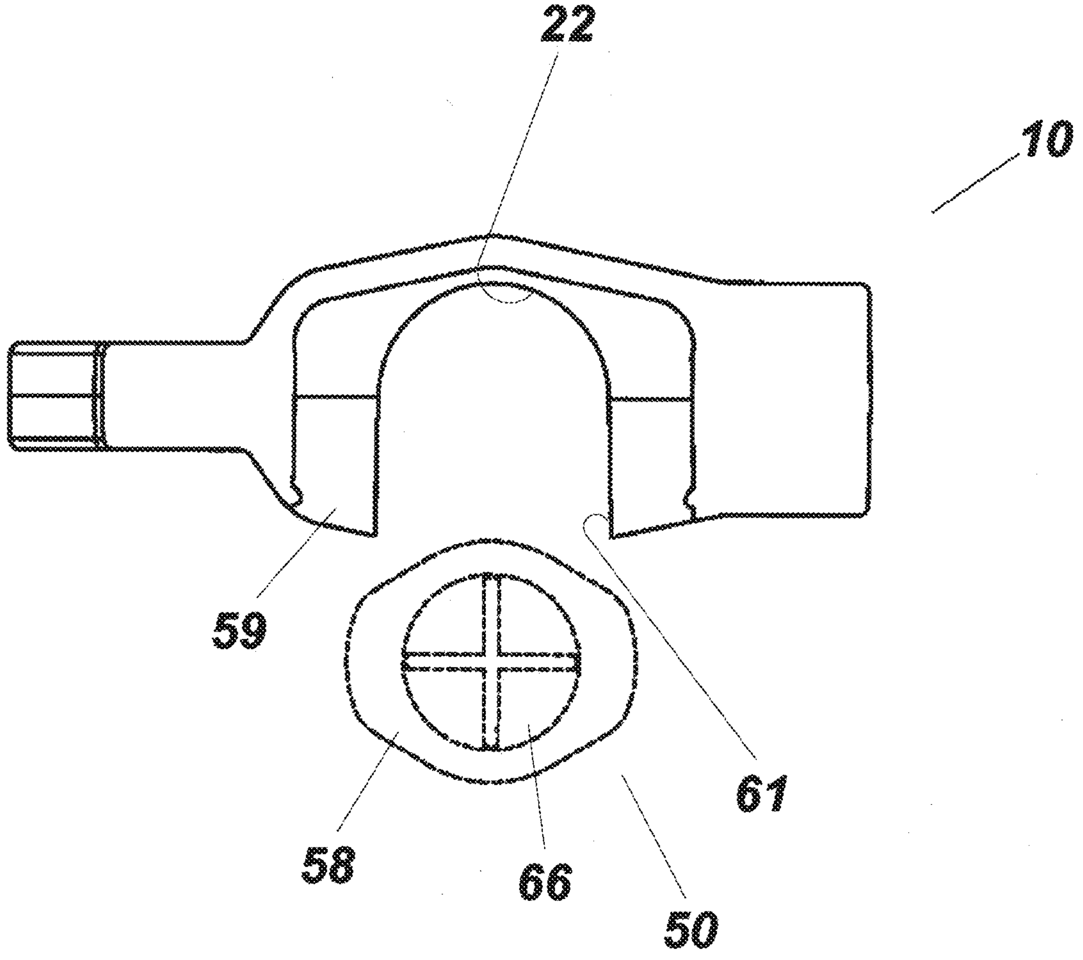
FIG. 6 is a side plane view of the syringe in position to be coupled to the hand grip adapter.
Figure 7:
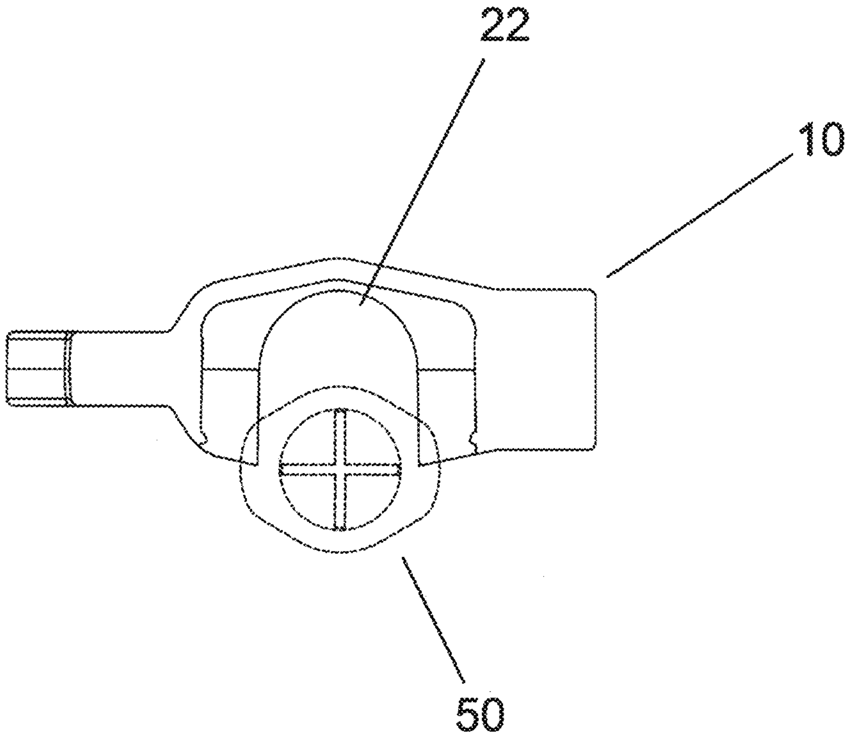
FIG. 7 is a side plane view of the syringe partially coupled to the hand grip adapter.
Figure 8:
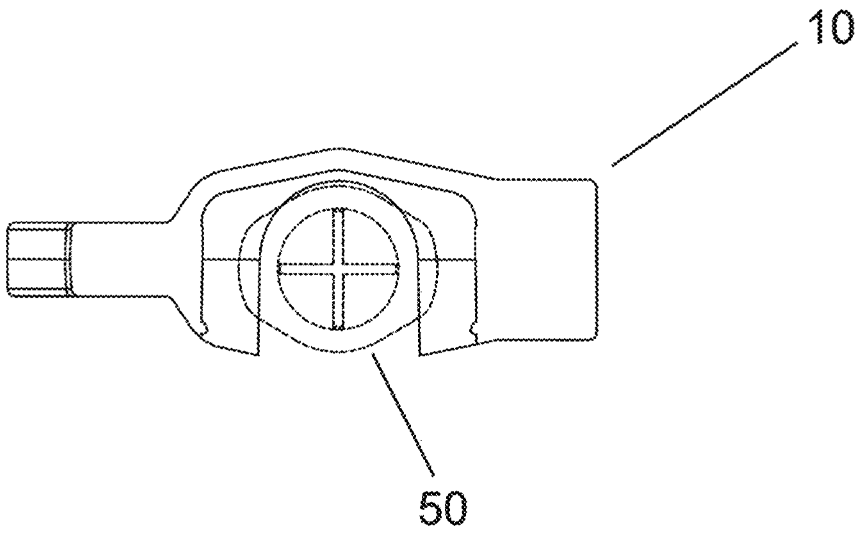
FIG. 8 is a side plane view of the syringe fully coupled to the hand grip adapter.

FIG. 6 is a top plane view of a syringe 50 available for placement into the hand grip adapter 10 illustrating different positions during assembly. The syringe 50 having a laterally extending flange 58 with the finger base 66 above the flange 58. The flange 58 is slidably insertable into the centrally dispose receptacle 22 having tabs 59, 61 on each side of the receptacle 22 for engaging an edge of the flange 58. FIG. 6 is a top plane view of the syringe 50 available for placement into the hand grip adapter 10; FIG. 7 is a top plane view of the syringe 50 about to be placed into the hand grip adapter 10 by passing the entry tabs 59, 61; and FIG. 8 is a top plane view of the syringe 50 coupled to the hand grip adapter 10 wherein the entry tabs 59, 61 inhibit removal by frictionally engaging the flange 58.

Figure 9:
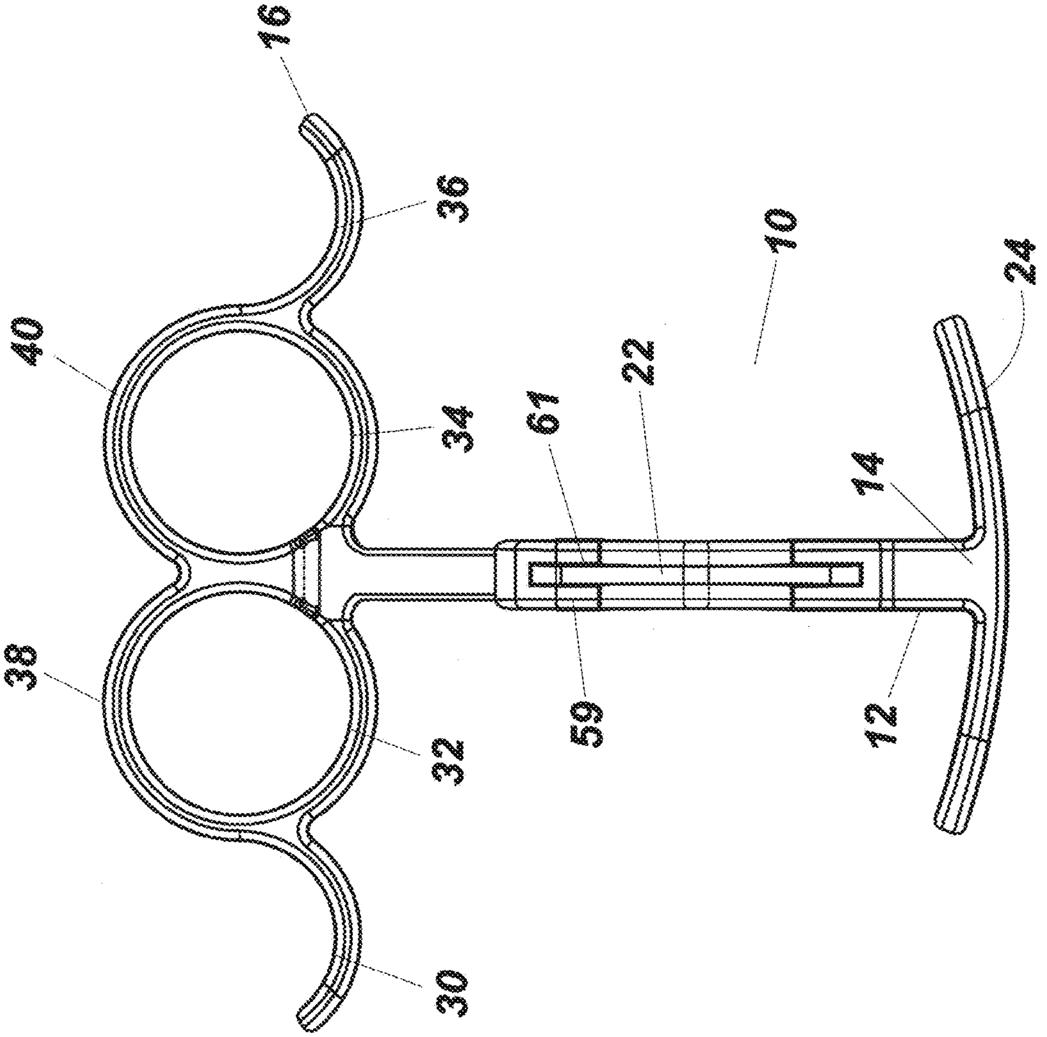
FIG. 9 is a side perspective view of the hand grip adapter without offset.
Figure 10:
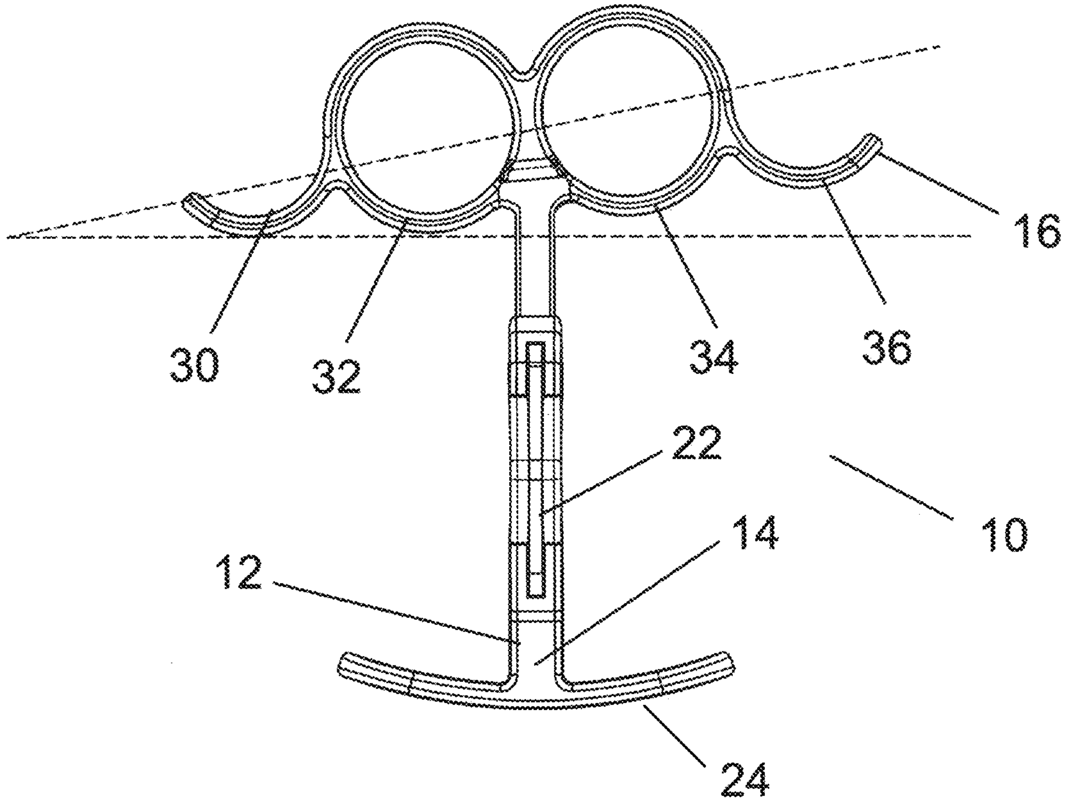
FIG. 10 is a side perspective view of the hand grip adapter with an offset noticeable by a angle depiction.

FIG. 9 is a side plane view of the hand grip adapter 10 without offset wherein the first end wall 14 is formed perpendicular to the support base 12 substantially parallel to the second end wall 16 forming depressions for receipt of the operator's fingers. FIG. 10 depicts the hand grip adapter 10 with an offset wherein the second end wall 16 is placed at an angle to the first end wall 14. In this embodiment the first depression 30 is at a separate elevation to the fourth depression 36 providing an offset.

Figure 4:
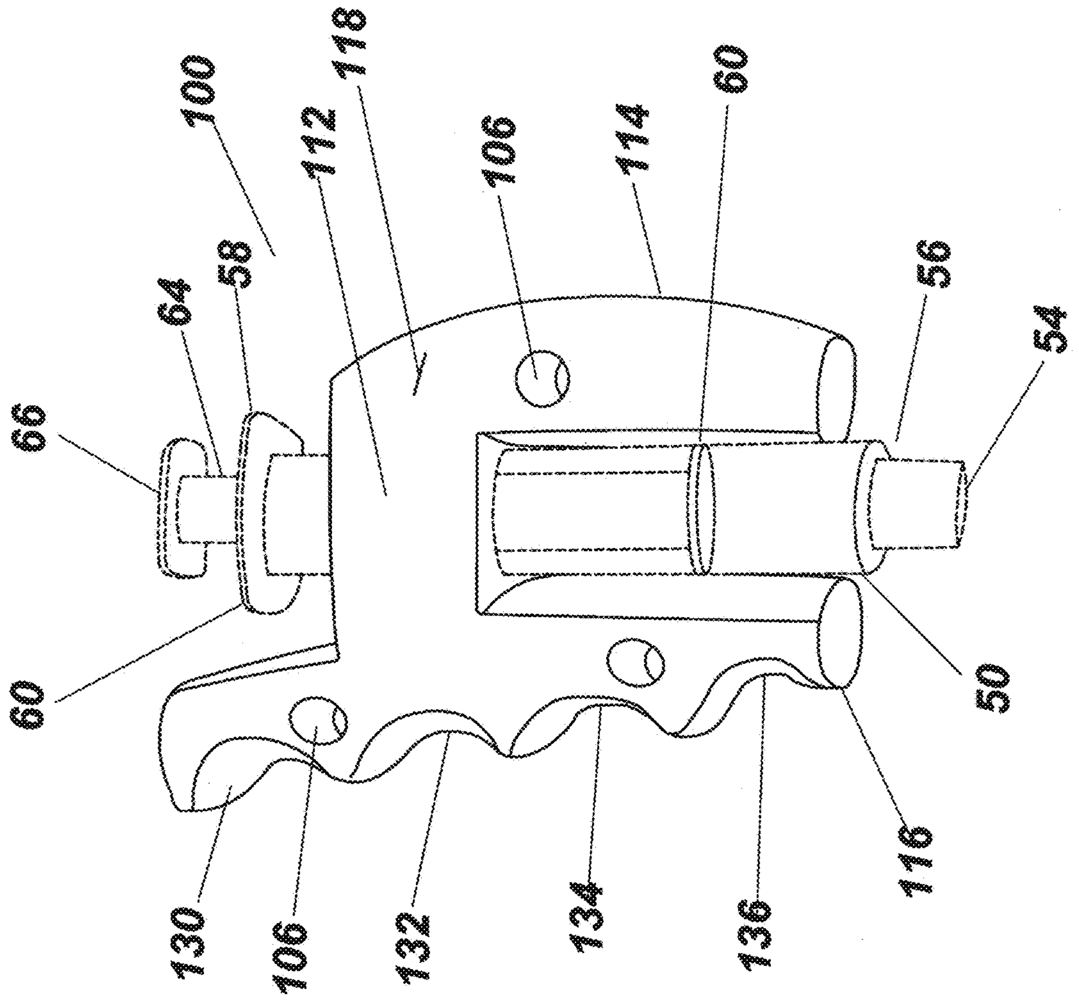
FIG. 4 is an alternative view of a hand grip adapter.
Figure 5:
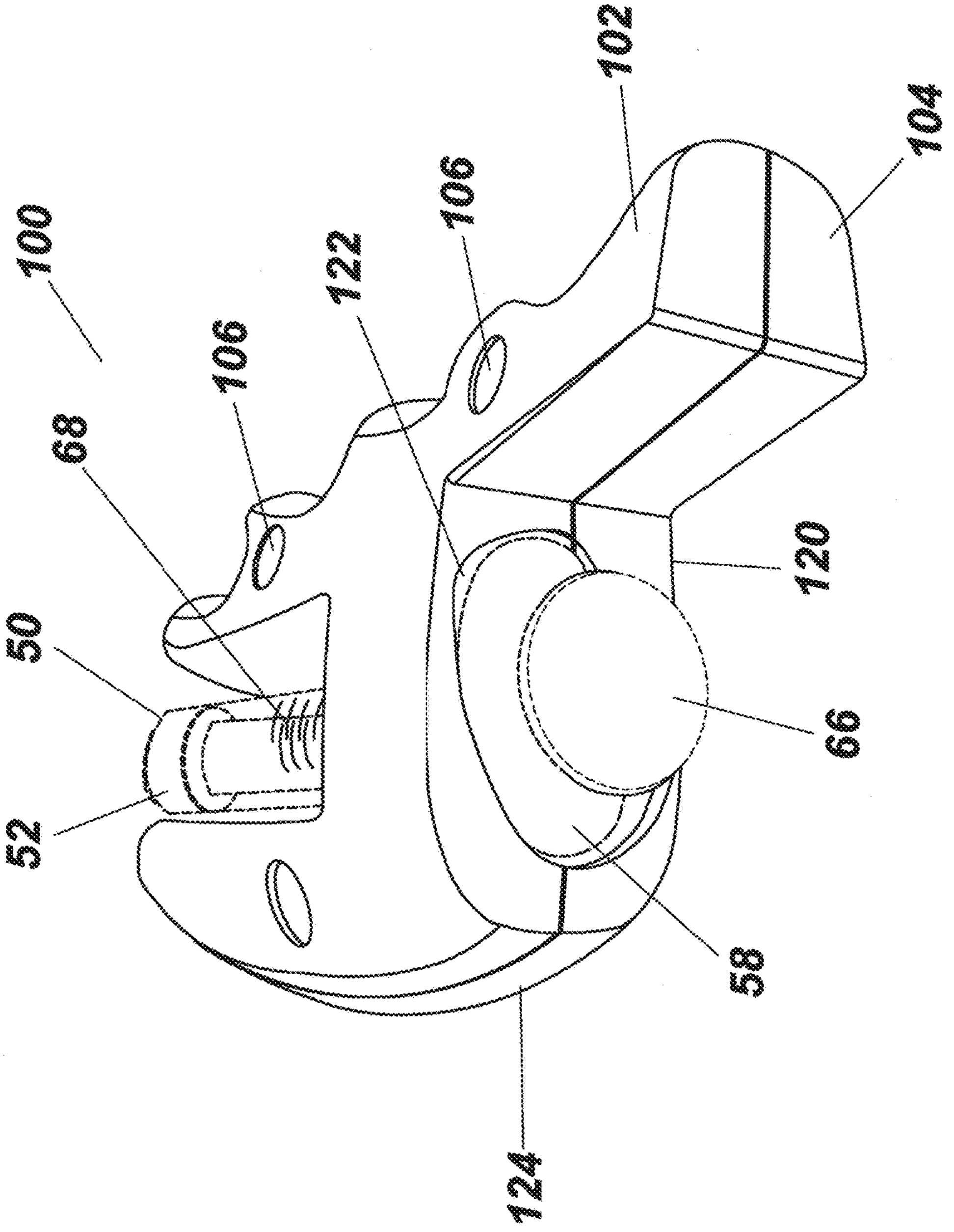
FIG. 5 is a top plane view of FIG. 4.

Referring now to FIGS. 4-5, illustrated is an alternative embodiment wherein the adapter 100 is composed of two halves 102, 104 that are held together using fasteners 106. In another embodiment the halves can be mounted together wherein the fasteners consist of press-fit or snap hook features.

The hand grip adapter 100 is used with a syringe 50 having an outlet 54 at one end 56 and a laterally extending flange 58 at the opposite end 60. A shaft 64 attached to the piston 62 and extending outwardly of the body 52 at the opposite end and operative to impart reciprocal movement to the piston 62, and a finger base 66 extending from the shaft 64.

The hand grip adapter 100 comprising a support base 112 between a first end wall 114, a second end wall 116, and opposing side walls 118, 120. The support base 112 has a receptacle 122 for receipt of a syringe 50 laterally extending flange 58. The first end wall 114 is formed perpendicular to the support base 112 having a curvature outer surface 124 that conforms to the palm of a human hand. The outer surface 116 is shaped to allow use by left or right handed individuals with a slight curvature that allows positioning in any size hand. The second end wall 116 is formed parallel to the first end wall 114 having an outer surface with a first depression 130 for receipt of an index digit, a second depression 132 for receipt of a middle digit, a third depression 134 for receipt of a ring digit; and a fourth depression 136 for receipt of a little digit. The first side wall 112 is configured to rest in the palm of an individual's hand and the second end wall 116 is configured to receive the finger tips from the individual's hand with a syringe 50 placed in the socket 122 therebetween. The individual may depress the finger base 66 with their thumb allowing a controlled injection of fluid from the syringe 50 and an uninterrupted view of dosage line 68 found on the side of the syringe 50.

The hand grip adapter provides greater control and increased ability to eject precise amounts of contrast agent volumes over the standard three-finger grip. The hand grip adapter is designed to be suitable for bulk manufacturing techniques such as injection molding with FDA and sterilization compliant plastics. To minimize the manufacturing cost and since the adapter is intended for one-time use only, all design features have been optimized to function correctly with the minimum amount of material and for an ease of manufacturing and assembly.

The novel aspects of this adapter include; an increased control for small volume ejection, an ease of conversion from three-finger grip to palm-held thumb control for any standard size 12 and 10 ml syringe, a simple twist-and-lock feature for securing the syringe in place, and a simplistic design that is suitable for immediate bulk manufacturing via injection molding. Additionally, with the wrist in the same position, the novel adapter allows the dosage lines to be in more natural view for interpretation in comparison to the three-finger grip which may contribute to a greater volume control even further. The adapter is low cost to manufacture and either is recycled or made of an autoclavable material such as polypropylene.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more elements, possesses those one or more elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A hand grip adapter for a syringe defined as a hollow cylindrical body having an outlet at one end and a laterally extending flange at the opposite end, a piston disposed within and adapted for reciprocal movement in the body, a shaft attached to the piston and extending outwardly of the body at the opposite end and operative to impart reciprocal movement to the piston, and a finger base extending from the shaft, the adapter comprising:

a support base having a first end wall spaced apart from a second end wall by a bridge therebetween, said bridge including a receptacle for receipt of the laterally extending flange of the syringe, said first end wall having a curvature outer surface formed perpendicular to said bridge, said second end wall including an outer surface with depressions;

wherein said hand grip adapter is constructed and arranged to gripped by an individual wherein said first side wall is positioned in the palm of the individual's hand and said depressions of said second end wall configured to receive the individual's index through pinky fingers wherein the individual's thumb is available to depress the syringe finger base, whereby the individual may depress the finger base using thumb carpometacarpal flexion allowing a controlled injection of fluid from the syringe.

2. The hand grip adapter for a syringe according to claim 1 including a rim member encompassing at least one finger depression forming a circular opening for receipt of a finger.

3. The hand grip adapter for a syringe according to claim 1 wherein said receptacle includes entry tabs to secure said syringe flange in said receptacle.

4. The hand grip adapter for a syringe according to claim 1 wherein said receptacle is formed on an end wall of said support base.

5. The hand grip adapter for a syringe according to claim 1 wherein said curvature outer surface of said first end wall is constructed and arranged to follow the curvature of the palm of a hand.

6. The hand grip adapter for a syringe according to claim 1 wherein said finger depressions are further defined as a wave surface for positioning four fingers of a hand.

7. The hand grip adapter for a syringe according to claim 1 wherein support base is constructed from recyclable plastic.

8. The hand grip adapter for a syringe according to claim 7 wherein plastic is polypropylene.

9. The hand grip adapter for a syringe according to claim 1 wherein said second end wall is formed substantially parallel to said first end wall.

10. The hand grip adapter for a syringe according to claim 1 wherein said second end wall is formed at an offset angle to said first end wall.

11. The hand grip adapter for a syringe according to claim 1 wherein said hand grip can be operated either left handed or right handed.

12. A hand grip adapter for a syringe defined as a hollow cylindrical body having an outlet at one end and a laterally extending flange at the opposite end, a piston disposed within and adapted for reciprocal movement in the body, a shaft attached to the piston and extending outwardly of the body at the opposite end and operative to impart reciprocal movement to the piston, and a finger base extending from the shaft, the adapter comprising:

a plastic support base formed integral to a first end wall and a second end wall and opposing side walls, said support base having a receptacle for frictional receipt of a laterally extending flange of the syringe and an aperture sized to pass the body of the syringe, said first end wall formed perpendicular to said support base having a curvature outer surface, said second end wall having an outer wave surface for receipt of the fingers of the hand;

wherein said first side wall is configured to rest in the palm of an individual's hand and said second end wall is configured to receive the finger tips from the individual's hand with a syringed placed in said body therebetween, whereby the individual may depress the finger base of the syringe using thumb carpometacarpal flexion for controlled injection of fluid from the syringe.

13. The hand grip adapter for a syringe according to claim 12 including at least one finger depression includes a rim forming a circular opening for placement of a finger.

14. The hand grip adapter for a syringe according to claim 12 wherein said support base is constructed of an autoclavable material.

15. The hand grip adapter for a syringe according to claim 12 wherein said finger depressions are curved surfaces for positioning four fingers of a hand.

16. The hand grip adapter for a syringe according to claim 12 wherein said receptacle is constructed and arranged to receive a size 12 ml or 10 ml syringe.

* * * * *